(12) United States Patent
Winter

(10) Patent No.: US 6,524,541 B1
(45) Date of Patent: Feb. 25, 2003

(54) CATALYST STRUCTURES

(75) Inventor: Manfred Winter, Dittelsheim-Hessloch (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/428,059

(22) Filed: Oct. 27, 1999

(30) Foreign Application Priority Data

Oct. 30, 1998 (DE) .......................................... 198 50 141

(51) Int. Cl.⁷ ............................................... B01J 21/00
(52) U.S. Cl. ........................ 422/222; 422/211; 422/221; 422/171; 422/177; 422/179; 422/180; 422/190; 502/527.11; 502/527.18; 502/527.19; 502/527.24
(58) Field of Search .......................... 422/41, 48, 221, 422/222, 171, 177, 179, 180, 190, 192; 428/71, 304.4; 425/403; 502/527.11, 527.14, 527.17, 527.18, 527.19, 527.2, 527.21, 527.22, 527.24

(56) References Cited

U.S. PATENT DOCUMENTS 4,162,993 A * 7/1979 Retallick .................... 502/439
5,672,324 A * 9/1997 Okamoto et al. ........... 422/174

* cited by examiner

Primary Examiner—Marian C. Knode
Assistant Examiner—Basia Ridley
(74) Attorney, Agent, or Firm—Keil & Weinkauf

(57) ABSTRACT

A molding (catalyst structure) for chemical apparatuses which is formed from at least two closed frames and one or more cross-pieces connecting these frames, where the frames are arranged at a distance from one another in a single plane or in a plurality of parallel planes about an (imaginary) molding (structure) axis which is perpendicular to the plane(s) and passes through the center points of the frames. The molding (catalyst structure) is preferably formed from at least four closed frames and one or more cross-pieces connecting these frames, where the frames are arranged one inside the other at a distance from one another in at least two parallel planes about an (imaginary) molding (structure) axis which is perpendicular to the planes and passes through the center points of the frames, and each plane has at least two frames.

15 Claims, 10 Drawing Sheets

CATALYST STRUCTURES

Heterogeneously catalyzed pyrolysis reactions, such as the pyrolysis of formylalanine nitrile (FAN) to vinylformamide and prussic acid, are usually carried out on loose beds of catalyst packing elements coated with the catalytically active substance. Such beds of packing elements have the disadvantage of relatively large pressure loss. In spite of identical depths of the catalyst bed, the pressure losses can vary, meaning that, on use of multi-tube reactors, different pressure losses in the individual reaction tubes can arise under certain circumstances. This can result in non-uniform temperature and residence time of the reactants in the individual reaction tubes, which can have an adverse effect on reaction conversion and reaction yield.

It is known that at temperatures >350° C., energy transport due to radiation increases greatly compared with thermal heat conduction in gases, meaning that at these temperatures, a high proportion of heat transfer takes place by radiation. However, beds of packing elements frequently have only low radiation transparency, meaning that a pronounced radial temperature profile can arise in the reaction tube. This problem has only been solved in part by use of substantially radiation-transparent packing elements, for example Hiflow rings. An unequal radial temperature distribution partly arises simply because the radiation intensity decreases with increasing radiation path. Correspondingly, in exothermic reactions, the temperature is the highest in the reactor core and the lowest in the immediate vicinity of the reactor wall, while in endothermic reactions, the reverse temperature conditions arise. However, different temperatures mean different reaction rates, with the consequence that radial concentration profiles of the starting material and product corresponding to the radial temperature profile can occur, which have an adverse effect on the reaction yield.

Reactor material and packing material have different coefficients of thermal expansion. During heating, the reaction tube expands, and the catalyst bed settles in the tube and is partially crushed by the tube during cooling thereof This catalyst fracture results in an increase in pressure loss, with the result that the bed must be changed frequently.

Packing elements of fragile material can, in addition, only be introduced into a water-flooded reactor, which means that filling of the reactor with the catalyst and replacement of the catalyst bed are complex. In the case of supported catalysts doped with water-soluble substances, such as the supported $Al_2O_3$ catalysts doped with potassium carbonate that are used for the pyrolysis of formylalanine nitrile, the doping can only take place in the reactor after the reactor has been filled with the catalyst packing elements, with drying being necessary before and after impregnation. This procedure is extremely complex.

It is an object of the present invention to provide catalyst structures (moldings) which do not have the abovementioned disadvantages.

We have found that this object is achieved by a molding (catalyst structure) for chemical apparatuses which is formed from at least two closed frames and one or more cross-pieces connecting these frames, where the frames are arranged at a distance from one another in a single plane or in a plurality of parallel planes about an (imaginary) molding axis which is perpendicular to the plane(s) and passes through the center points of the frames.

The frames can be arranged in a single plane or in a plurality of parallel planes, where a plurality of frames arranged in the same plane are arranged at a distance from one another and one inside the other. In one embodiment, the molding is formed from at least three frames arranged in at least two parallel planes. For example, one plane may have two frames lying one inside the other, with a further plane having only one frame.

Preference is given to a molding for chemical apparatuses which is formed from at least four closed frames and one or more cross-pieces connecting these frames, where the frames are arranged one inside the other at a distance from one another in at least two parallel planes about an (imaginary) molding axis which is perpendicular to the planes and passes through the center points of the frames, and each plane has at least two frames.

Chemical apparatuses are, for example, tubular reactors, tube-bundle reactors, distillation columns or gas scrubbers. The moldings according to the invention can be used therein as catalysts, catalyst supports or packing elements which promote heat and/or mass transfer.

The closed frames, cross-pieces or the entire molding can have a compact, porous or other structure. For example, the frames can be hollow inside. The closed frames can have any desired geometry.

The frames can have a circular geometry. Closed frames having a circular geometry are also referred to as rings. Closed frames having a geometry other than circular are thus structures corresponding to rings which have another geometry instead of circular.

The frames can have a geometry which is delimited exclusively by curved lines. Besides circular geometry, the frames can have, for example, an oval geometry.

The frames can have edges and corners. The frames can have, for example, the geometry of polygons. Polygons are triangles, quadrangles, pentagons, etc.

The frames can have, for example, star-shaped geometry or the geometry of a rosette (wave line closed in a circular manner).

The frames preferably have essentially the extension of the tube cross section, a certain play being necessary during insertion of the molding (catalyst structure) into the reaction tube. Through corresponding choice of the frame geometry, the molding can be matched to the cross section of the reaction tube.

In general, but not necessarily, reaction tubes have a circular cross section. Preferred frame geometries are therefore those whose periphery is delimited by a circle. Preferred frames having a polygonal geometry are therefore those whose corners are on an arc.

Particularly preferred frames have high symmetry. Particularly preferred frames having a polygonal geometry therefore have the geometry of regular polygons. Regular polygons are squares, triangles, pentagons, hexagons, etc., having sides of equal length. Of these, particular reference is given to frames having at least 5 sides.

Particular preference is given to frames having a circular geometry (rings).

In a preferred embodiment of the moldings (catalyst structures) according to the invention, the frames of adjacent planes are not congruent with respect to an (imaginary)

parallel shift along the common axis of the frames. The incongruence of the frames counters the formation of laminar flow profiles in the reaction tube and thus promotes mass transfer in the radial direction.

The frames are incongruent, for example, if they have different shapes. Thus, one plane can have hexagonal frames and the plane above or below can have pentagonal or hexagonal frames. The frames are also incongruent if, although having the same geometry and size, they are each oriented differently in the planes. For example, adjacent planes can have frames of regular hexagonal geometry which are rotated by an angle of between 1° and 59° with respect to one another.

The frames are also incongruent if, although having the same geometry and orientation, they have different sizes. In a preferred embodiment of the moldings according to the invention, frames of identical geometry, but decreasing size, with no two frames having the same size, are oriented the same way in each of two planes, but are arranged in the sequence of size alternately in the upper and lower of the two planes. Particular preference is given to an arrangement in which the frames in adjacent planes are arranged on gaps, i.e. the size of the frames differs in such a way that a frame in one plane is arranged above or below the gap formed by the next-largest and next-smallest frame in the plane above or below.

The moldings (catalyst structures) according to the invention have at least two frames per plane. The moldings can have the same number or a different number of frames in each plane, but preferably have the same number of frames in each plane. They particularly preferably have at least three, in particular at least four frames in each plane.

The separations between the frames in a plane having three or more frames can be identical or different. In a preferred embodiment, the separations between the frames are identical. In a flow reactor, moldings (catalyst structures) having equidistant frames produce a constant pressure loss distributed over the cross section of the reaction tube. The flow rate and residence time in the center and in the peripheral zones of the reaction tube are thus essentially the same.

In a further preferred embodiment, the separation of the frames in a plane decreases from the outside inward. Such moldings produce a higher pressure loss in the center of the reaction tube than in the peripheral regions. The flow rate in the center of the tube is thus lower and the residence time greater than in the peripheral regions of the tube.

In a further preferred embodiment, the separation of the frames in a plane increases from the outside inward. Such moldings produce a lower pressure loss in the center of the reaction tube than in the peripheral regions. The flow rate in the center of the tube is thus higher and the residence time lower than in the peripheral regions of the tube.

Through an appropriate choice of the separations between the frames in a plane, a residence-time spectrum can thus be established which compensates for the effect of a radial temperature profile on the progress of the reaction at various points of the reactor cross section. Thus, in exothermic reactions, the temperature in the center of the reaction tube can be higher than in the peripheral regions since heat conduction takes place via the tube wall. In reactions having a positive activation energy, the reaction rate in the center is thus also higher. In this case, the use of moldings (catalyst structures) according to the invention with separations between the frames increasing from the outside inward means that the higher reaction rate in the center is at least partially compensated by a shorter residence time of the reactants, countering the formation of radial concentration profiles. In endothermic reactions, conversely, the temperature in the center of the reaction tube is lower than in the peripheral regions since heat supply takes place via the tube wall. In reactions having a positive activation energy, the reaction rate in the center is then lower. In this case, the use of moldings having separations between the frames decreasing from the outside inward means that the lower reaction rate in the center is at least partially compensated by a longer residence time of the reactants.

In reactions whose reaction rate is essentially temperature-independent, the use of moldings (catalyst structures) having equidistant frames may be advantageous.

A temperature rising from the periphery to the center of the reaction tube, and the consequent increase in reaction rate, is also countered by the entire frame surface area per reactor volume decreasing from the outside inward in moldings (catalyst structures) having a frame separation increasing from the outside inward—for a constant circumference of the frame cross section. Thus, in frames coated with a catalytically active substance, the contact area and thus the activity of the catalyst decreases from the outside inward. Furthermore, thermal radiation is absorbed more strongly by the frames which have a lower separation, i.e. are more densely arranged, in the peripheral regions of the reaction tube than in the center of the reaction tube owing to the larger contact area for thermal radiation there, which enables a temperature profile which is more balanced overall to be achieved.

The reduction in reaction rate caused by a temperature decreasing from the periphery to the center of the reaction tube is correspondingly countered by the overall frame surface area per reactor volume increasing from the outside inward in moldings (catalyst structures) having a frame separation decreasing from the outside inward—for a constant frame cross section. Thus, in frames coated with a catalytically active substance, the contact area and thus the activity of the catalyst increases from the outside inward. Furthermore, thermal radiation is absorbed less strongly by the frames which have a greater separation, i.e. are less densely arranged, in the peripheral regions of the reaction tube than in the center of the reaction tube owing to the smaller contact area for thermal radiation there, which enables a temperature profile which is more balanced overall to be achieved.

In a particularly preferred embodiment, the separation between the frames in a plane either increases or decreases from the outside inward in each plane.

In a further preferred embodiment of the moldings (catalyst structures), the circumference of the frame cross section either increases or decreases from the outside inward, the extension of the frame cross section in the direction of the molding axis particularly preferably also increasing or decreasing. An increasing circumference of the frame cross section increases the contact area of the catalyst or the contact area for thermal radiation per reactor volume. An increase or decrease in the circumference of the frame cross section from the outside inward thus acts precisely like a decrease or increase in the frame separation from the outside inward.

In a further preferred embodiment, the moldings (catalyst structures) have equidistant frames with a circumference of the frame cross section increasing from the outside inward. Such moldings are advantageously employed for carrying out endothermic reactions. In a further preferred embodiment, the moldings have equidistant frames with a circumference of the frame cross section decreasing from the outside inward. Such moldings are advantageously employed for carrying out exothermic reactions.

In a particularly preferred embodiment, the moldings (catalyst structures) have frames with a frame separation decreasing and a circumference of the frame cross section increasing from the outside inward. Such moldings are particularly advantageously employed for carrying out endothermic reactions. In a further particularly preferred embodiment, the moldings have frames with a frame separation increasing and a circumference of the frame cross section decreasing from the outside inward. Such moldings are particularly advantageously employed for carrying out exothermic reactions.

The frames can have a cross section of any desired shape. In general, the cross section of the frames has a simple shape, preferably that of a circle, an ellipse, a drop, an egg, a rectangle having rounded corners, a triangle, a parallelogram, a diamond, a rectangle or square, or a polygon having five or more sides.

A rectangle having rounded corners has, in the extreme case, a shape which can be thought of as composed of a rectangle and semicircles with a diameter corresponding to the side length which are placed on opposite sides of this rectangle. Rectangles having rounded corners are also all transitional shapes between this extreme shape and a rectangle.

In a preferred embodiment, the cross sections of the frames have an oblong shape with longitudinal and transverse axes which can be differentiated from one another. Examples are cross-sectional areas in the form of an ellipse, an egg, a rectangle having rounded corners, a rectangle (with the exception of a square), a diamond or a parallelogram. In the cases of symmetrical cross-sectional areas mentioned by way of example, the longitudinal axis is in the plane of symmetry of the areas.

The frames can all have the same or different cross sections. In the case of moldings (catalyst structures) having a circumference of the cross-sectional area increasing (decreasing) from the outside inward, the outermost (innnermost) frame in a plane can have a circular cross section and the other frames to the inside (outside) can have an elliptical or egg-shaped cross section or the cross section of a rectangle having rounded corners, the extension of the frame cross section in the direction of the molding axis increasing (decreasing) from the outside inward.

In a further preferred embodiment, the frame cross sections are inclined with respect to the molding axis. Inclined frame cross sections have an oblong cross section with a longitudinal axis and a transverse axis, where the longitudinal axes are inclined by an angle of from 1 to 45° with respect to the molding axis. The inclination of the frame cross sections additionally counters the formation of laminar flows and additionally promotes mixing of the reaction gases.

The inclination of the frame cross sections can be regular or irregular. The inclination is irregular if, for example, the frame cross sections are inclined to the right and to the left in irregular sequence.

The frame cross sections are preferably inclined in a regular manner. The frame cross sections are inclined in a regular manner if the frame cross sections are, for example, inclined alternately to the right and to the left in a plane in regular sequence.

In a particularly preferred embodiment of the moldings (catalyst structures), in a section plane containing the molding axis and cutting the frames perpendicularly, the frame cross sections in one plane are, in each case on one side of the molding axis, inclined in the same direction (to the right or to the left) and the frame cross sections in adjacent planes are inclined in the opposite direction. In this case, the frame cross sections in a plane can be inclined in the same direction on opposite sides of the molding axis or in opposite directions on opposite sides. The last-described embodiment can be implemented, for example, through the use of concentric, conically tapering rings having an oblong cross section which are arranged in a plane with the tapering side facing downward and in the adjacent planes with the tapering side facing upward.

The moldings (catalyst structures) can in principle have as many planes as desired. For reasons of simpler producibility, the moldings generally have precisely two planes.

The moldings (catalyst structures) according to the invention have cross-pieces connecting the frames. In principle, the cross-pieces can have any desired number and arrangement so long as the cross-pieces are arranged in such a way that adequate stability of the moldings is produced. The cross-pieces are preferably arranged in the axial direction. The cross-pieces can each connect all the frames or only some of the frames. For example, the moldings can have two, three, four or more cross-pieces running from the outermost to the innermost frame and each connecting all the frames in all planes. The moldings can have, for example, cross-pieces of which some each connect only the outer and central frames of the planes and others connect only the central and inner frames of the planes. The cross-pieces can also have, for example, a U-shape, where each arm of the U only connects the rings of one plane and the base of the U connects adjacent planes.

In a preferred embodiment, the moldings (catalyst structures) have cross-pieces which each connect all frames and cross-pieces which each connect only some of the frames, the extension of the cross-pieces to the inside being essentially delimited by the innermost frames. The delimitation of the cross-pieces by the innermost frames allows them to be introduced into a tubular reactor particularly easily by means of a rod reaching through the innermost frames. This makes it unnecessary to fill the reactor with water before introduction of the moldings into the reactor.

In a particularly preferred embodiment, the extension of the moldings in the direction of the molding axis is delimited on the underside by the cross-pieces and on the upper side by the frames. In the stacked state, the moldings thus rest on the underside with the frames on the upper side of the cross-pieces of the respective underlying molding, ensuring good stability. The dimensions of the cross-pieces are preferably such that an equidistant arrangement of all planes of all moldings is produced in the stacked state.

The moldings according to the invention can be made of all materials also used for the production of packing elements. Examples are ceramic materials, such as stoneware, porcelain and sintered corundum, metallic materials, such as carbon steel, stainless steel, titanium, nickel, copper and aluminum, or plastics, such as polypropylene, high-density polyethylene, polyvinyl chloride and polyvinylidene difluoride.

In the moldings according to the invention, the problem of catalyst fracture caused by crushing naturally does not occur.

The moldings according to the invention can be used as packing elements in distillation columns or in gas scrubbers.

The moldings according to the invention are preferably used as catalyst moldings. The moldings according to the invention used as catalyst moldings can be made entirely of any desired catalytically active substances or coated with any desired catalytically active substances. They can be employed for catalysis of any desired heterogeneously catalyzed gas-phase reactions or liquid-phase reactions.

For example, $Al_2O_3$ moldings impregnated with potassium carbonate can be used as catalyst moldings for the pyrolysis of formylalanine nitrile to vinylformamide and prussic acid or of formamide to water and prussic acid in a tubular reactor.

The present invention also relates to a process for the pyrolysis of formylalanine nitrile or formamide in a tubular reactor in the presence of an $Al_2O_3$ molding according to the invention doped with potassium carbonate.

The moldings according to the invention can be produced by all known processes for the production of packing elements. For example, the moldings can be produced by injection molding, powder injection molding or pressing processes, such as press sintering.

The moldings can be produced in one piece or in the form of two or more segments which can be joined together. The invention thus also relates to moldings according to the invention which can be assembled from two or more segments.

Segments are obtained by (imaginary) cuts from the periphery to the axis of the moldings. Segments are, for example, halves, thirds, quarters, etc., of the moldings.

The invention is illustrated in greater detail by FIGS. 1 to 9, which show specific embodiments of the moldings.

BRIEF DESCRIPTION OF THE DRAWINGS

FIG. 1 shows a plan view of a molding, the totality of which is designated by (1).

Figure 1:
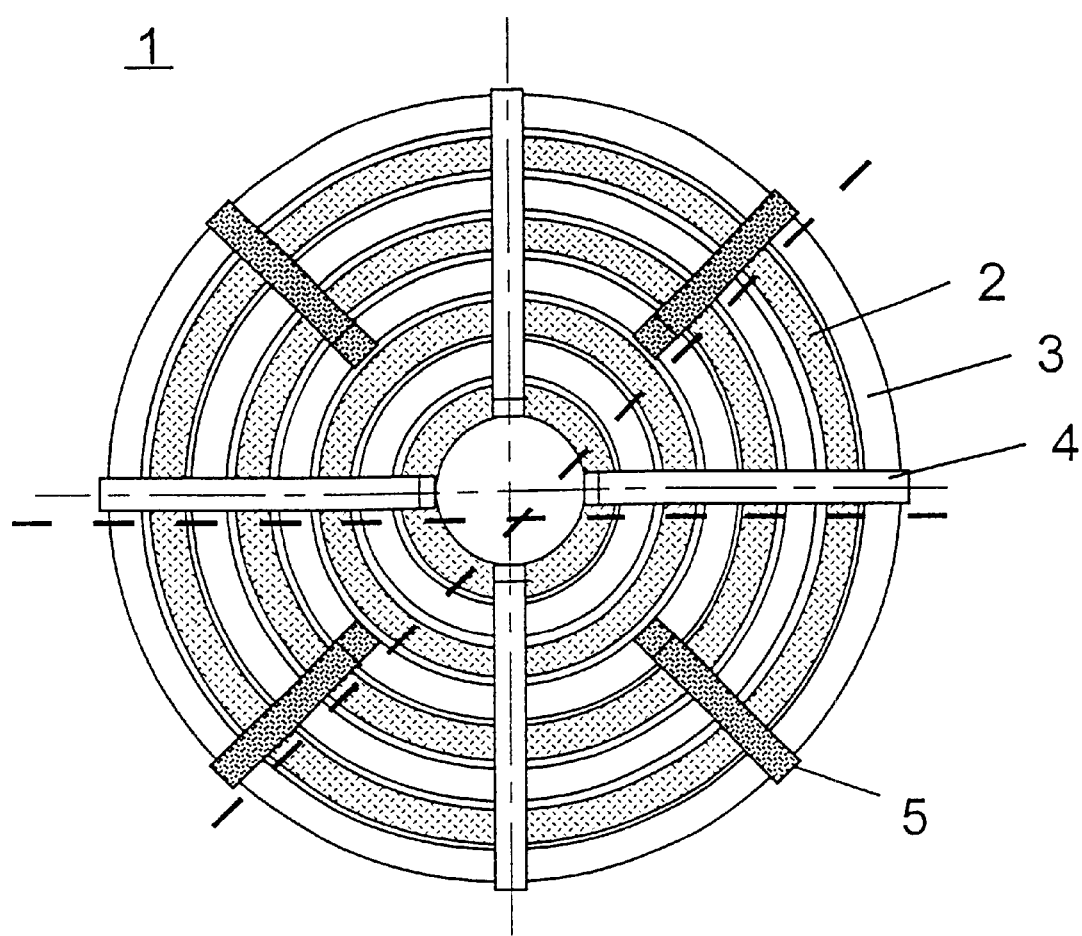
FIG. 1 shows plain view of a molding (catalyst structure) in accordance with the present invention.

The molding (1) has a total of four concentric rings (2) arranged in an upper plane and a total of four concentric rings (3) with an elliptical cross section arranged in a lower plane. The molding furthermore has a total of four cross-pieces (4), each of which connects all rings in the two planes, and a total of four cross-pieces (5), each of which connects the three outer rings in the two planes.

Figure 2:
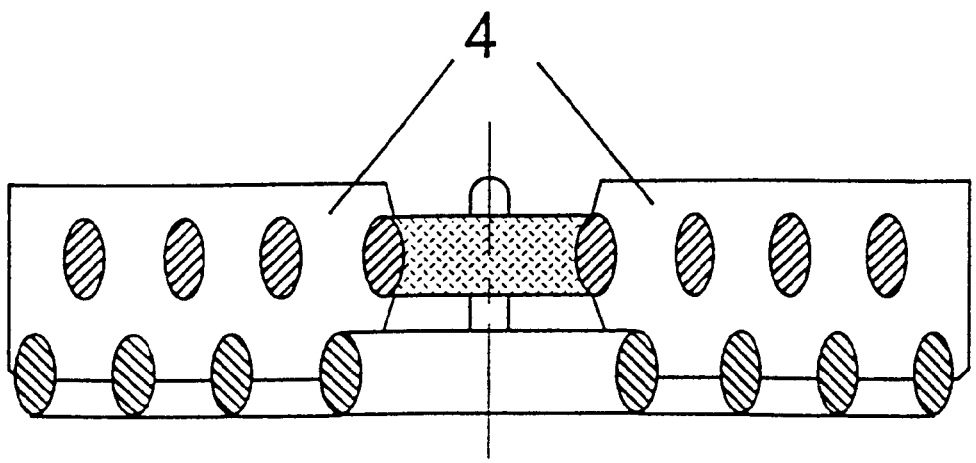
FIGS. 2–9 show specific embodiments of moldings (catalyst structures) in accordance with the present invention.

FIG. 2 shows a section through a molding (1) along the cross-pieces (4).

Figure 3:
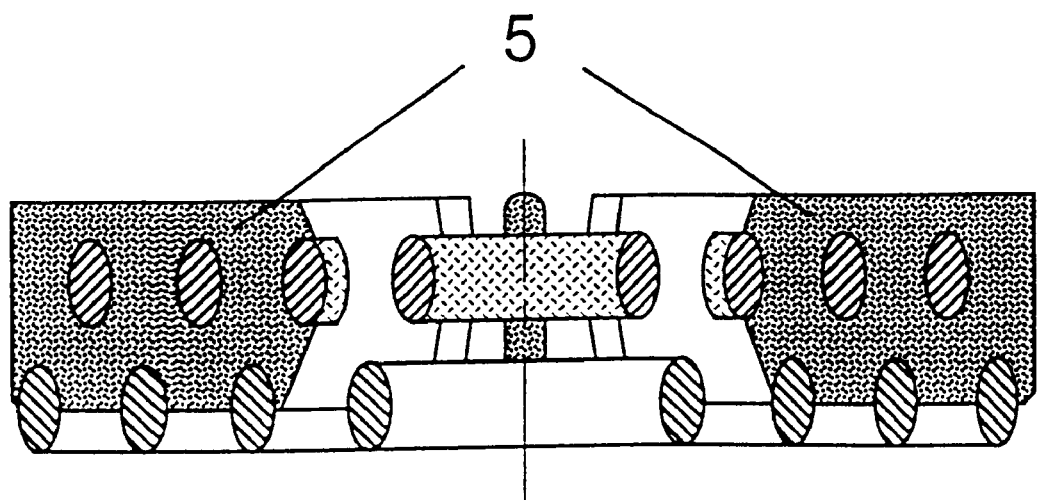

FIG. 3 shows a section through the molding (1) along the cross-pieces (5).

Figure 4:
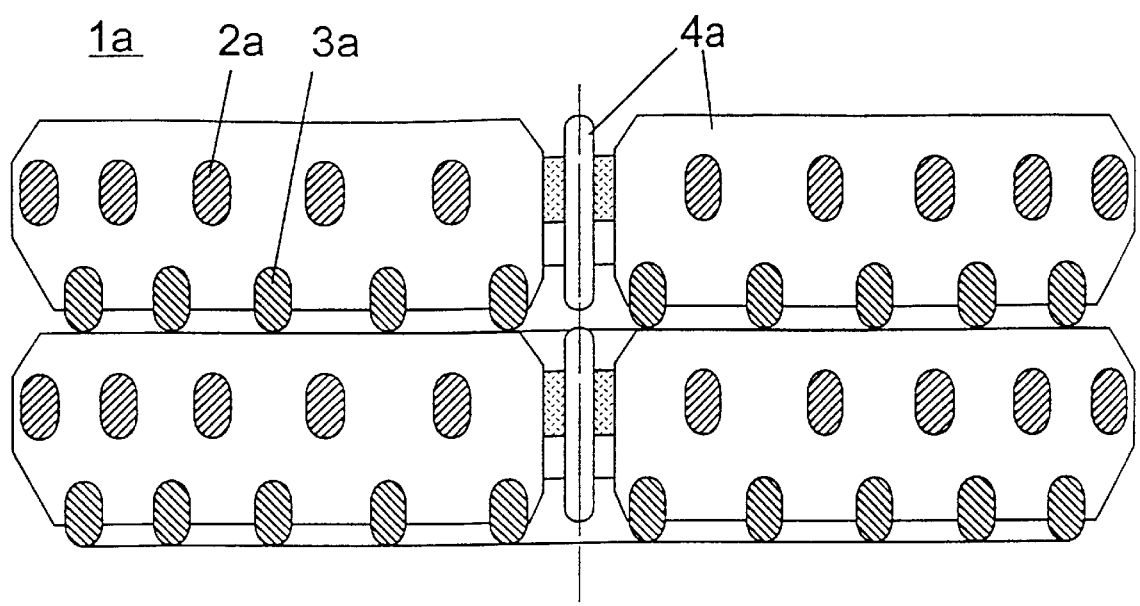

FIG. 4 shows a section along the cross-pieces (4a) through two further stacked moldings, the totality of which is designated by (1a), with frames (2a) and (3a) with separations increasing from the outside inward. The frame cross section has the shape of a rectangle having rounded corners.

Figure 5:
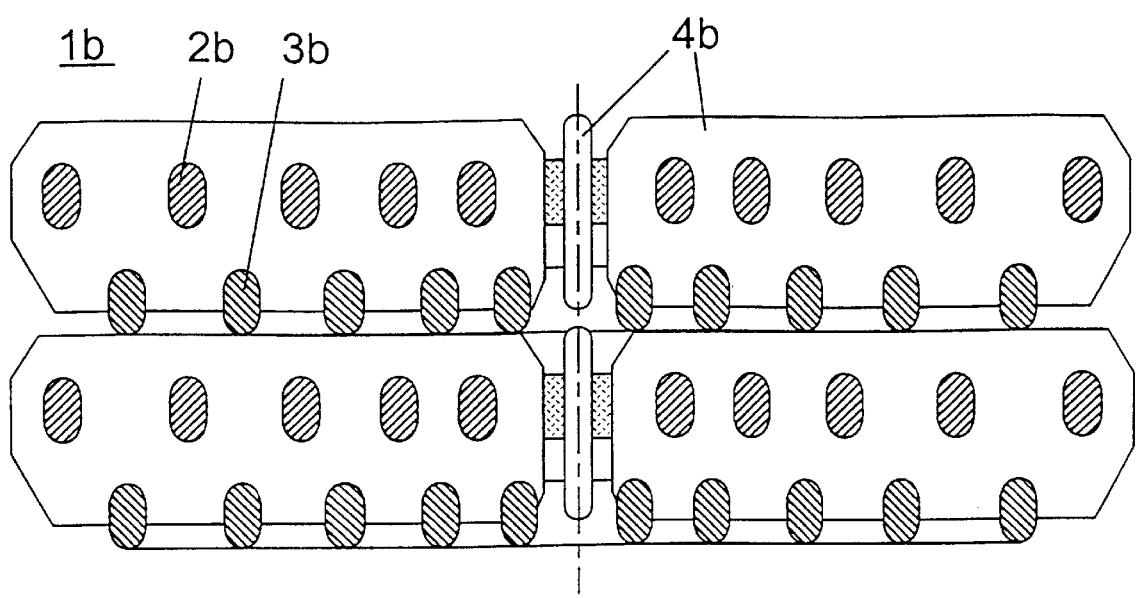

FIG. 5 shows a section along the cross-pieces (4b) through two further stacked moldings, the totality of which is designated by (1b), with frames (2b) and (3b) with separations increasing from the outside inward.

Figure 6:
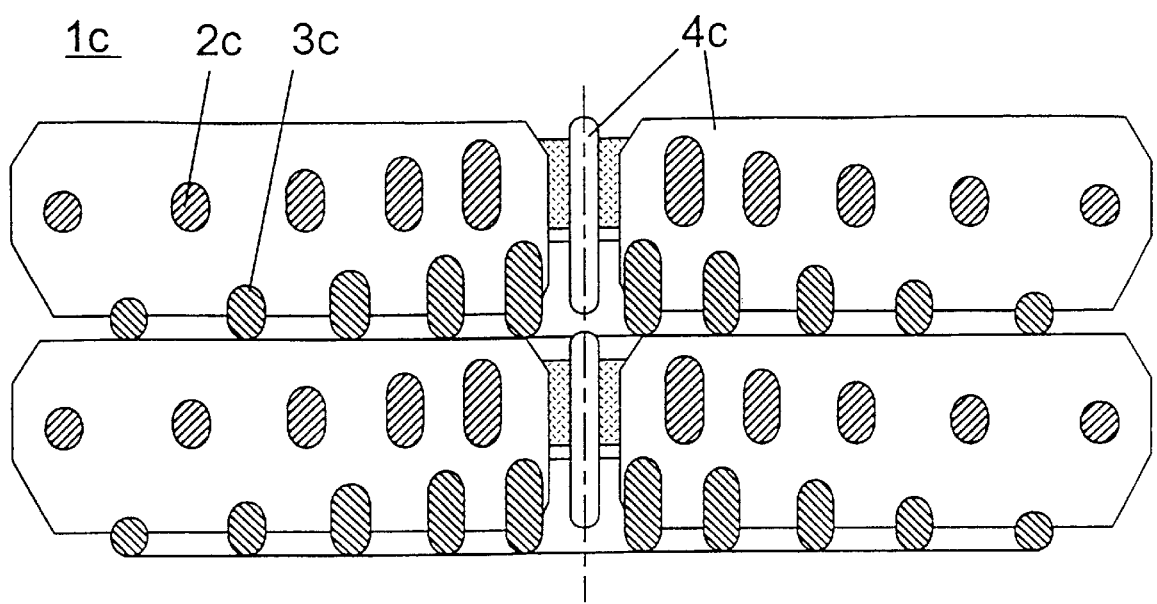

FIG. 6 shows a section along the cross-pieces (4c) through two further stacked moldings, the totality of which is designated by (1c), with frames (2c) and (3c) with separations decreasing from the outside inward and a circumference and axial extension of the frame cross section increasing from the outside inward.

Figure 7:
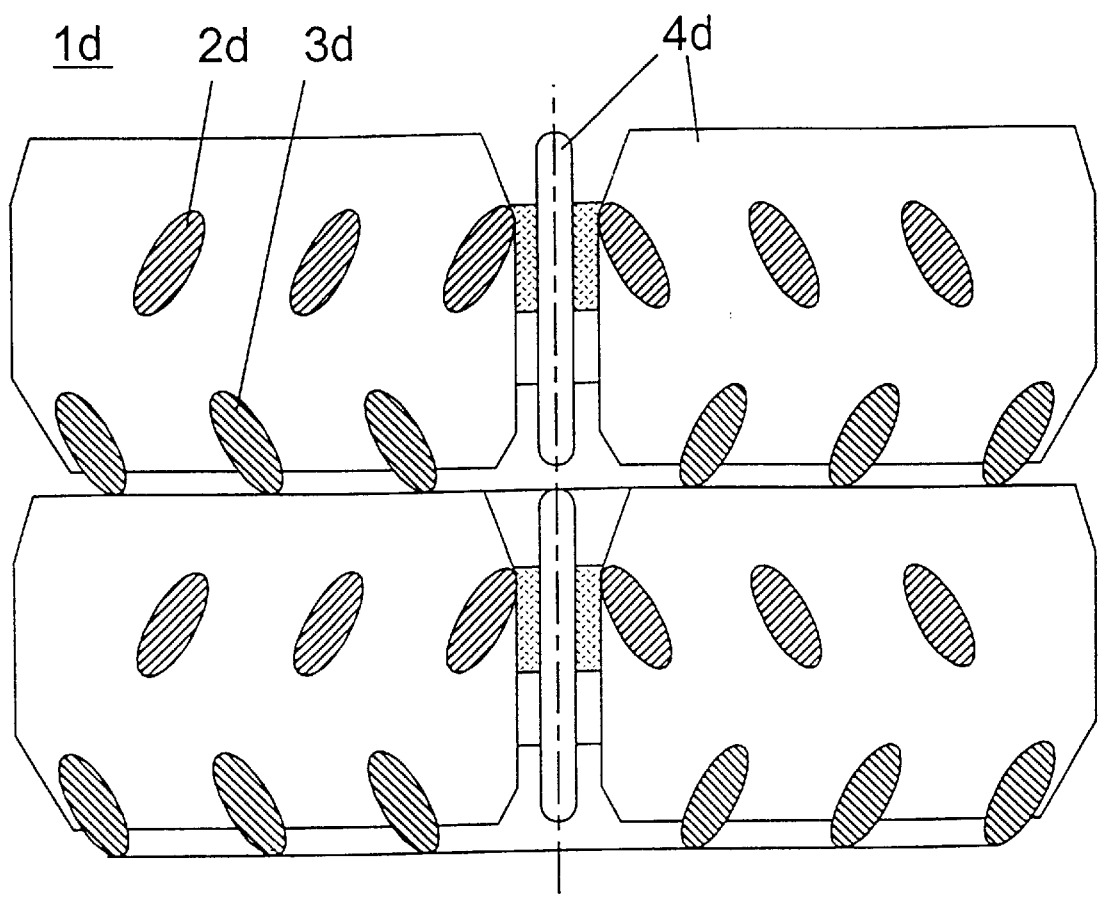
Figure 8:
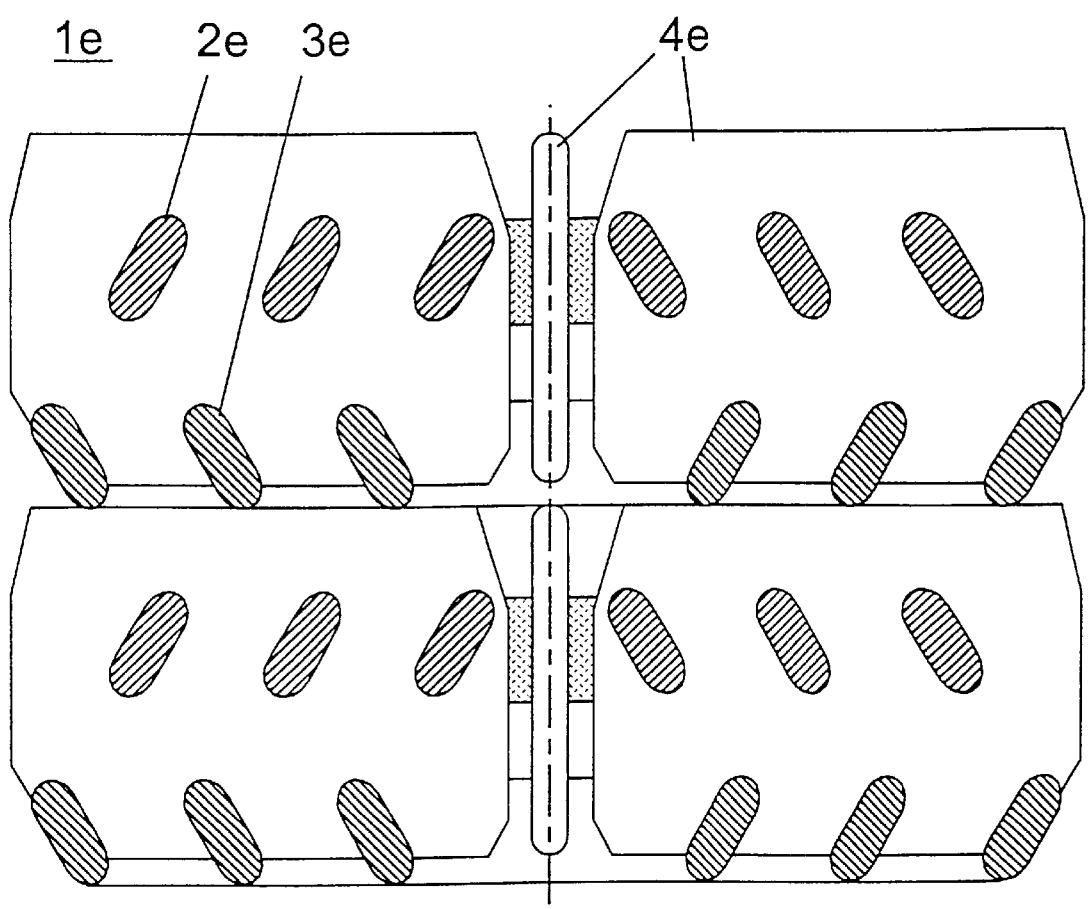
Figure 9:
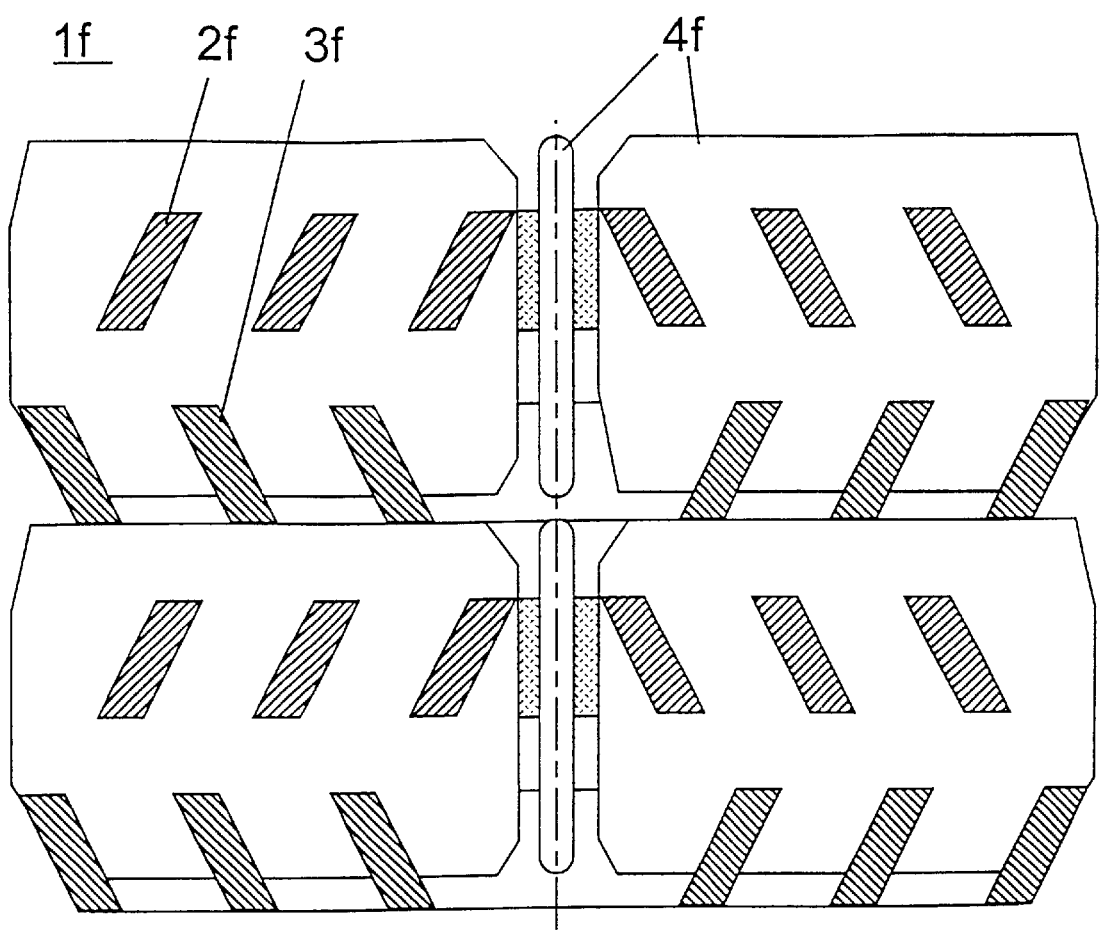

FIGS. 7 to 9 each show sections along the cross-pieces (4d), (4e) and (4f) respectively through further moldings stacked in pairs, the totality of which is designated by (1d), (1e) and (1f) respectively, with frames (2d), (2e) and (2f), and (3d), (3e) and (3f) respectively, with oblong cross sections inclined in different directions with respect to the molding axis. The cross sections of the frames (2d) and (3d), (2e) and (3e), and (2f) and (3f) respectively are examples of an elliptical cross section, a rectangular cross section having rounded corners and a trapezoidal cross section.

Figure 10:
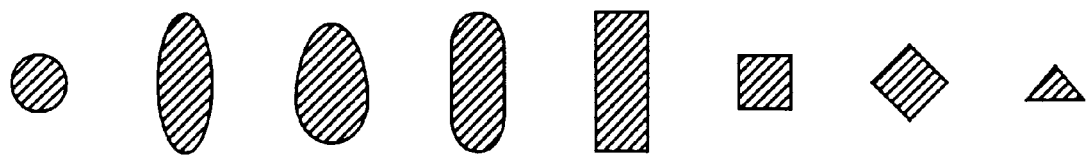
FIG. 10 shows exemplary frame cross sections in accordance with the present invention.

FIG. 10 shows possible frame cross sections by way of example. These have (from left to right) a circular geometry, an oval geometry, an egg-shaped geometry, a rectangular geometry having rounded corners, a rectangular geometry, a square geometry, a diamond-shaped geometry and a triangular geometry.

I claim:

1. A catalyst structure for chemical apparatuses, wherein said catalyst structure is formed from at least four closed frames and one or more cross-pieces connecting said at least four frames, wherein said at least four frames are arranged one inside another at a distance from one another in at least two parallel adjacent planes about a structure axis, wherein said structure axis is perpendicular to said at least two planes and wherein said structure axis passes through center points of said at least four frames, and wherein each of said at least two planes has at least two frames.

2. The structure as claimed in claim 1, wherein frames in adjacent planes are not congruent with respect to a parallel shift along the structure axis.

3. The structure as claimed in claim 1, wherein said at least four frames have identical shape with no two frames having equal diameters, and wherein said at least four frames are arranged in sequence of their diameters alternately in upper and lower of two adjacent planes having the same orientation in said two adjacent planes.

4. The structure as claimed in claim 1, wherein each plane has at least three frames and wherein separation between said at least three frames in said each plane either increases of decreases from outside inward of said each plane.

5. The structure as claimed in claim 1, wherein each plane has at least two frames, and wherein circumferences of cross sections of said at, least two frames in said each plane increase from outside inward of said each plane.

6. The structure as claimed in claim 1, wherein each plane has at least two frames, and wherein circumferences of cross sections of said at least two frames in said each plane decrease from outside inward of said each plane.

7. The structure as claimed in claim 1, wherein said at least four frames have a circular geometry or a polygonal geometry.

8. The structure as claimed in claim 1, wherein shape of cross sections of said at least four frames is selected from the group consisting of a circle, an ellipse, a drop, an egg, a rectangle having rounded corners, a triangle, a parallelogram, a diamond, a rectangle, a square and a polygon having five or more sides.

9. The structure as recited in claim 1, wherein each of said at least four frames has oblong cross section with a longitudinal axis and a transverse axis, wherein said longitudinal axes are inclined by an angle of from 1 to 89° with respect to the structure axis.

10. The structure as claimed in claim 9 further comprising a section plane containing said structure axis and cutting said at least four frames perpendicularly, wherein the cross sections of all frames in a first of said at least two planes on one side of said section plane have the longitudinal axes which are inclined in one direction and the cross sections of all frames in a second of said at least two planes, adjacent to said first of said at least two planes, on the same side of said section plane are inclined in direction opposite to said one direction.

11. The structure as claimed in claim 1 comprising first cross-pieces connecting all of said at least four frames and second cross-pieces connecting only some of said at least four frames, wherein extensions of all of the first and second cross-pieces in direction towards center of said structure are essentially delimited by innermost frames.

12. The structure as claimed in claim 1, wherein an extension of said structure in the direction of the structure axis is delimited on one side by cross-pieces and on the other side by frames.

13. The structure as claimed in claim 1, wherein said structure can be assembled from two or more segments.

14. The structure as claimed in claim 1, wherein said structure is made entirely of a catalytically active substance or is coated with a catalytically active substance.

15. The structure as claimed in claim 1, wherein said structure is made of $Al_2O_3$ and impregnated with potassium carbonate.

* * * * *